United States Patent [19]

Kuipers

[11] Patent Number: Plant 7,713

[45] Date of Patent: Nov. 12, 1991

[54] *NEOREGELIA CAROLINAE* PLANT NAMED DEVROE

[75] Inventor: Nico J. Kuipers, De Kwakel, Netherlands

[73] Assignee: Reginald Deroose, Belgium

[21] Appl. No.: 520,354

[22] Filed: May 7, 1990

[51] Int. Cl.[5] ..... A01H 5/00

[52] U.S. Cl. ..... Plt./88

[58] Field of Search ..... Plt./88, 88.8

[56] References Cited

U.S. PATENT DOCUMENTS

P.P. 3,971 11/1976 Coster et al. ..... Plt. 88

*Primary Examiner*—Howard J. Locker

*Attorney, Agent, or Firm*—Foley & Lardner

[57] ABSTRACT

A new cultivar of Neoregelia named Devroe characterized by its rosette type and relatively large size and upright leaves; long variegated leaves which have green margins and light yellow and green striations or bands between the margins; excellent leaf production to form a full plant; a bright red socket in the middle of the rosette, in which appear light purple flowers.

4 Drawing Sheets

The present invention comprises a new and distinct cultivar of neoregelia plant, botanically known as *Neoregelia carolinae* and referred to by the cultivar name Devroe.

The new cultivar is a mutation of the cultivar Flandria, and was discovered by the inventor in 1982 in a greenhouse in De Kwakel, The Netherlands, growing among plants of the parent cultivar. The mutation was recognized due to its totally different leaf color and marking.

Subsequent asexual reproduction by the inventor by taking shoots of the newly discovered plant has demonstrated that the combination of characteristics as herein disclosed for the new cultivar are firmly fixed and are retained through successive generations of asexual reproduction.

The following traits have been repeatedly observed and in combination distinguish Devroe as a new and distinct cultivar:

1. The plant is relatively large and rosette in form.
2. Devroe has an abundance of leaves (approximately 50) and is approximately 60–70 cm in overall diameter when fully grown.
3. The leaves of Devroe are erect, with little or no drooping or downward curvature except at the leaf tips. The leaves are slightly concave at their attachment to the rosette, and are otherwise essentially flat.
4. The leaves are relatively long (approximately 30 cm), are prickly at the margins, and variegated. Each leaf is striated with green and light yellow bands, with the marginal sections of the leaf being a dark green.
5. Several very short and relatively wide leaves form a socket at the center of the plant in which purple flowers are formed. The short leaves are bright red except for the outer leaf margins and tips which are green. The immediately underlying leaves are infused with varying amounts of red, most heavily near the center.

The following observations, measurements and values describe plants grown in De Kwakel, The Netherlands under greenhouse conditions which closely approximate those generally used in horticultural practice. Color references are made to The Royal Horticultural Society (RHS) Color Chart, except where general color terms of ordinary significance are used. The color values were determined between 8:30–9:00 on Jan. 7, 1988 under bright but slightly cloudy daylight conditions at Aalsmeer, The Netherlands.

In the color photographic drawings, Sheet 1 comprises a side elevational view of a potted plant of Devroe, showing the upright leaf habit. Sheet 2 is a top plan view of Devroe. Sheet 3 comprises two comparison photographs of Devroe and the parent cultivar Flandria. The photograph at the top is a side view showing Flandria at the left and Devroe at the right. The bottom photograph is a top plan view showing Devroe on the left and Flandria on the right. Sheet 4 comprises two comparison photographs of Devroe and the comparison cultivar Perfecta Tricolor. The top photograph is a side elevational view showing Devroe on the left and Perfecta Tricolor on the right. The bottom photograph comprises a top plan view showing Perfecta Tricolor on the left and Devroe on the right. The plants illustrated in the several photographs are of the same age, thirteen (13 months).

Devroe can be compared to its parent cultivar Flandria and to the cultivar Perfecta Tricolor. With regard first to Flandria, the leaf shape and inflorescence are similar. Devroe differs from Flandria by its more erect, non-drooping leaves which form a much more erect plant, its greater abundance of leaves which forms a more full plant, and by its completely dissimilar leaf color and marking. In Devroe, the leaf margins are green, and in the interior there are green and light yellow lengthwise bands of varying width. In Flandria, the leaf margins are very light yellow and the interior almost a solid dark green (see Sheet 3 of the photographic drawings).

Devroe and Perfecta Tricolor have similar leaf shapes and generally similar leaf variegation. However, the leaves of Perfecta Tricolor droop or downwardly bend very pronouncedly (see Sheet 4 of photographic drawings), the rosettes of Devroe is a much more intense red than the rosette of Perfecta Tricolor, and the inflorescence socket of Devroe is much greater in diameter (approximately 4 cm) than the socket of Perfecta Tricolor (approximately 2 cm) whereby the purple inflorescence of Devroe is much more pronounced.

Classification:

*Botanical.*—*Neoregelia carolinae* cv Devroe.

*Commercial.*—Neoregelia.

Parentage: A spontaneous mutation of the parent Flandria.

Asexual propagation: By shoots.

Plant: From 20 cm to 25 cm tall when grown in 13 cm pots, and approximately 60 cm in diameter when fully grown.

Grown habit.—Excellent, very vigorous.

Leaves:

*Form.*—Elongated, extending into rosette at center, and aristate.

*Size.*—Length: Approximately 30 cm. Width (at middle): 5–6 cm.

*Texture.*—Mainly palisade parenchyma and spongy parenchyma.

*Veins or ribs.*—Cannot be distinguished by the human eye.

*Number.*—Approximately 50.

*Color.*—Upper surface: Leave margins and interior bands darker than 147A, with narrow green bands between bright yellow bands (approximately 3C) being lighter in varying degrees and difficult to measure precisely by color value. By comparison, the relatively wide leaf margins of Flandria are a more gold-yellow 10B-C, while the interior leaf color is 147A, but lighter than Devroe. Flandria has minimal striating or banding interiorly of the edges (see Sheet 3), and the banding is approximately the same color as the margins when it does occur. In Devroe, the interior banding is a much brighter yellow and infused in varying degrees with green, thereby providing a totally different effect than the parent. Lower surface: Generally similar although somewhat lighter.

Rosette:

*Leaves forming socket.*—Leaves forming socket are very short and 5–6 cm wide.

*Color (RHS).*—45C-D, with red infusion in regions of certain leaves immediately surrounding rosette. Red interior gradually fades and is generally confined, except for a few leaves, to a radius of 8–9 cm of center of rosette.

*Flowers.*—Arrangement: Small flower head. Color: Relatively purple, 76A-B (flowers not in bloom in color photographs). Fruit: Insignificant. Duration of Flowers: 2–3 months.

Reproductive organs:

*Stamens.*—Filament: White. Anthers: Light yellow.

*Pistils.*—Stigma: White. Style: White. Ovary: White.

Disease resistance: No disease problems noted to date.

I claim:

1. A new and distinct cultivar of *Neoregelia carolinae* named Devroe, as described and illustrated.

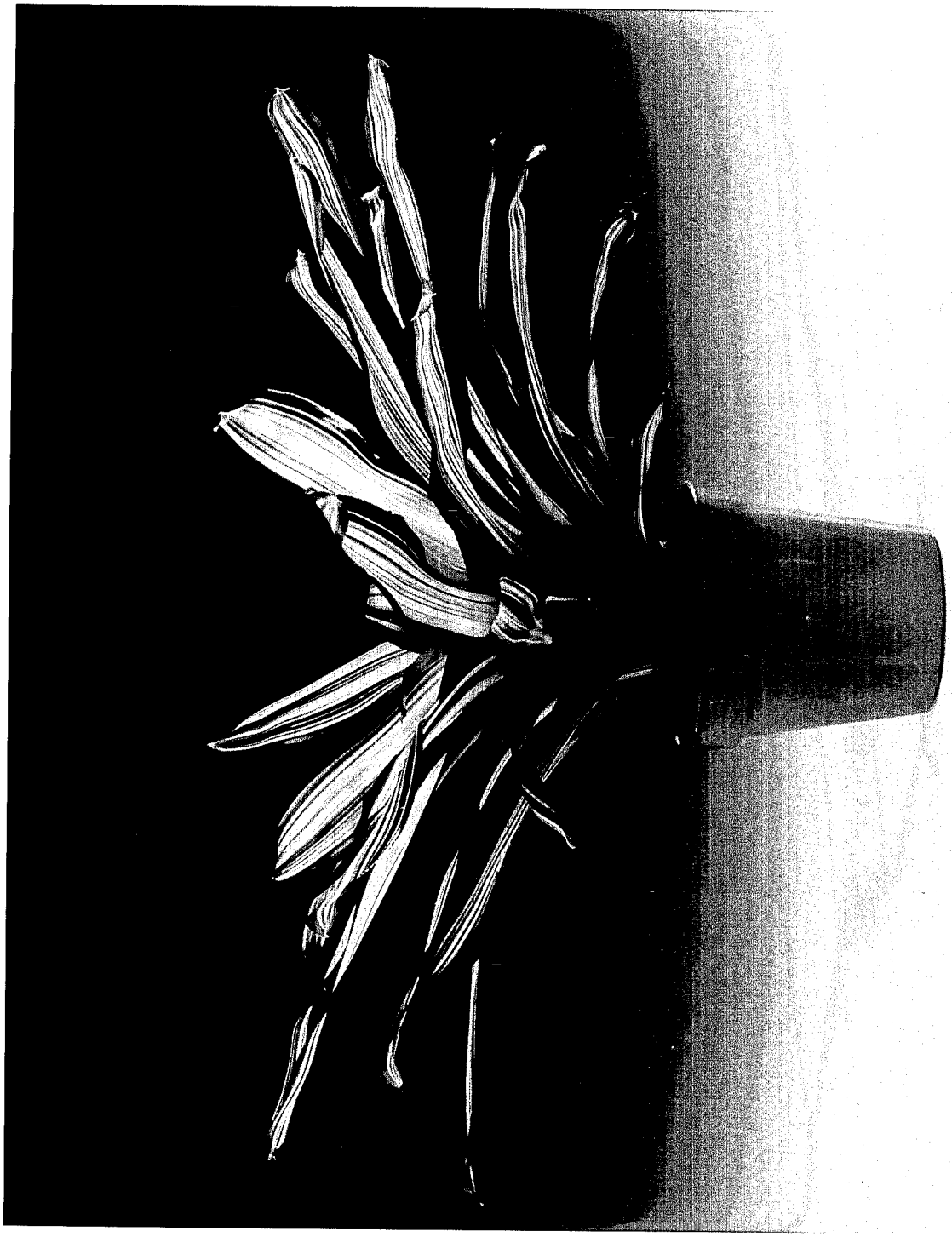

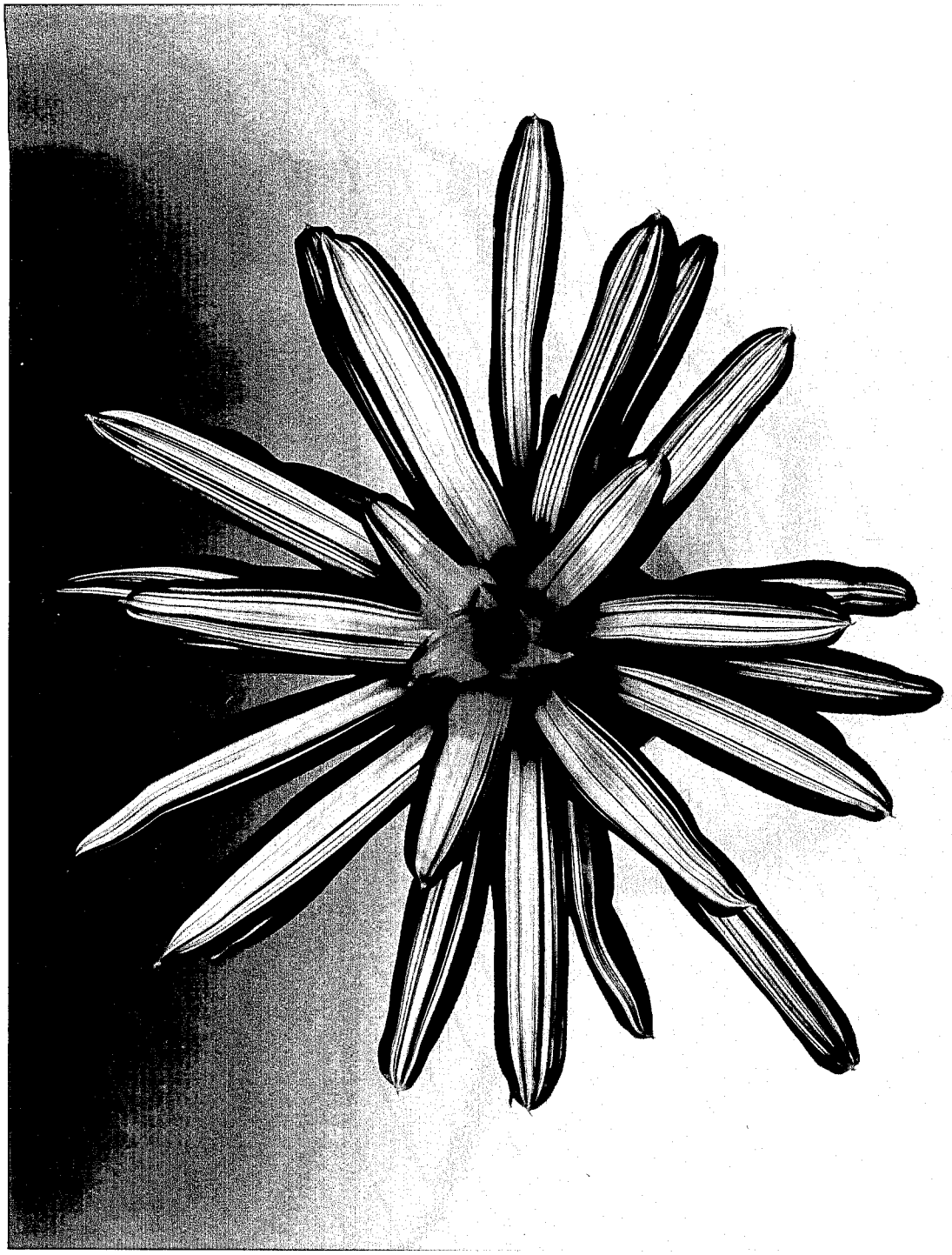

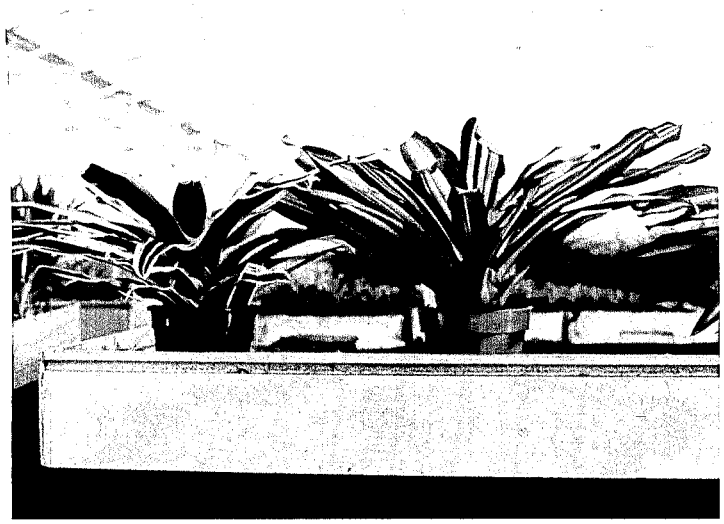
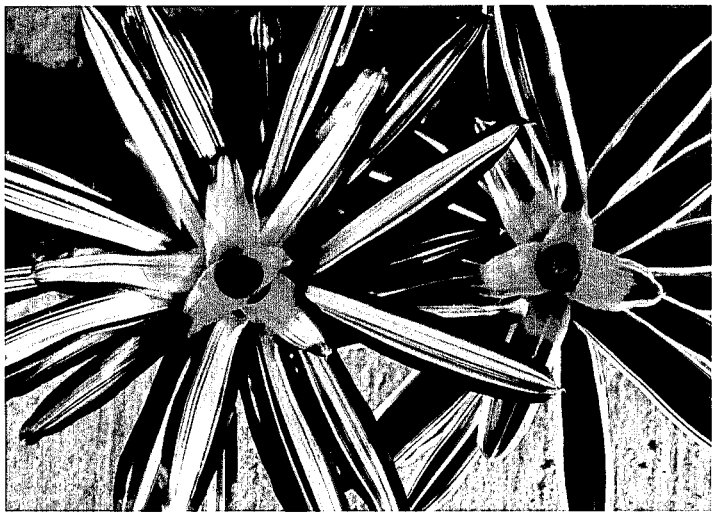

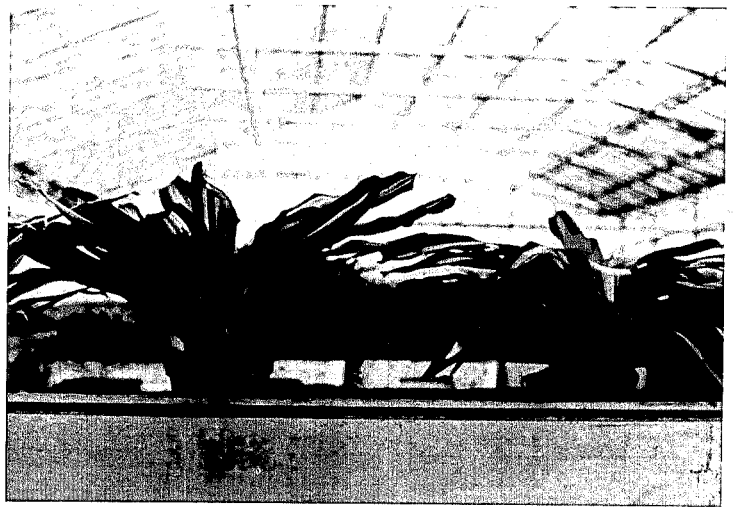
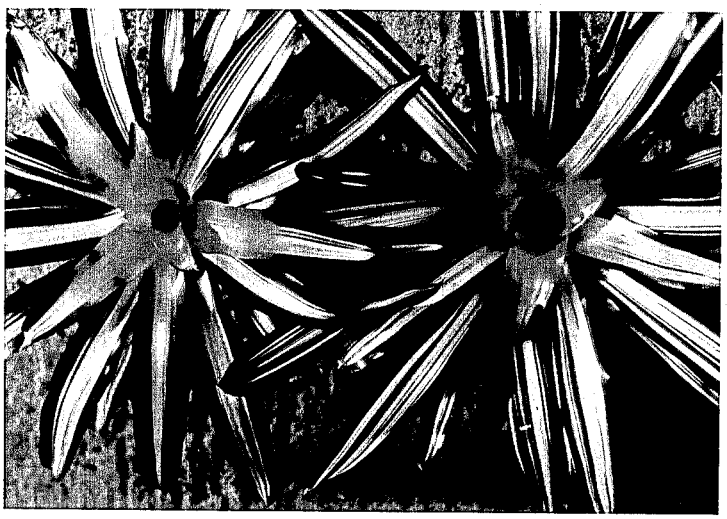

* * * * *